(12) United States Patent
Werle et al.

(10) Patent No.: US 7,531,652 B2
(45) Date of Patent: May 12, 2009

(54) PROCESS FOR PREPARATION OF SOLID TRIS (2,3-DIBROMOPROPYL) ISOCYANURATE

(75) Inventors: Peter Werle, Gelnhausen (DE); Manfred Schmidt, Gelnhausen (DE)

(73) Assignee: Evonik Degussa GmbH, Essen (DE)

( * ) Notice: Subject to any disclaimer, the term of this patent is extended or adjusted under 35 U.S.C. 154(b) by 302 days.

(21) Appl. No.: 11/200,419

(22) Filed: Aug. 10, 2005

(65) Prior Publication Data
US 2006/0036068 A1    Feb. 16, 2006

(30) Foreign Application Priority Data
Aug. 14, 2004    (DE) .................. 10 2004 039 490

(51) Int. Cl.
*C07D 251/34*    (2006.01)
*C08J 3/14*    (2006.01)
*B32B 27/00*    (2006.01)

(52) U.S. Cl. ...................................... 544/192; 524/101
(58) Field of Classification Search ................ 544/192
See application file for complete search history.

(56) References Cited

FOREIGN PATENT DOCUMENTS

JP    07173092    *    7/1995

* cited by examiner

*Primary Examiner*—Venkataraman Balasubramanian
(74) *Attorney, Agent, or Firm*—Michael A. Sanzo; Law Office of Michael A. Sanzo, LLC

(57) ABSTRACT

The present invention is directed to a process for the isolation of tris(2,3-dibromopropyl)isocyanurate. The process uses an adsorbent which promotes easy conversion into a solid form of TDPI. The invention also includes to the solid TDPI product prepared in this way and its use in providing flame retardancy to plastics.

20 Claims, No Drawings

PROCESS FOR PREPARATION OF SOLID TRIS (2,3-DIBROMOPROPYL) ISOCYANURATE

CROSS REFERENCE TO RELATED APPLICATIONS

The present application claims priority to German application DE 10 2004 039 490.3, filed on Aug. 14, 2004, the contents of which is hereby incorporated by reference.

FIELD OF THE INVENTION

The invention is directed to a process for the isolation of tris(2,3-dibromopropyl)isocyanurate. Isolation involves conversion to a solid, easily filterable, form from an organic product solution with addition of a porous, absorbent material.

BACKGROUND

Tris(2,3-dibromopropyl)isocyanurate ("TDPI") is a very effective flame retardant with high thermal stability. It is used mainly to provide flame retardancy to polypropylene and also to polyethylene and polystyrene. Advantages of TDPI are its low viscosity, low tendency towards discoloration and low corrosivity in relation to process tooling.

The first process for the preparation of TDPI was described in 1972 in DE 2244543. This application describes the synthesis of brominated triallyl isocyanurate [CAS No. 1025-15-6], using dichloromethane as solvent. After bromine has been added, the reaction product is precipitated via addition of petroleum ether, and filtered. The filter cake is triturated with MeOH and washed with water. This procedure—reaction in a, preferably, chlorinated solvent and precipitation of TDPI via addition of a non-solvent—is also described in many more recent patent applications.

JP 2000053658 decribes a proceedure in which triallyl isocyanurate is brominated in dichloromethane and methanol is used as a precipitatant. JP 1999228549 discloses a reaction medium composed of a mixture of heptane and dichloromethane and in which heptane is used for precipitation.

JP 2000053658 mentions not only dichloromethane but also reaction solvents such as 1,1,1-trichloroethane, chloroform, carbon tetrachloride, ethylene dichloride, dibromomethane and others. Among the precipitants listed are: methanol, ethanol, isopropanol, pentane, hexane, cyclohexane. In order to remove excess bromine (colour reduction) the reaction solution is also treated with an aqueous hydrazine solution.

In all of these processes, fundamental problems arise from the physical properties of TDPI and from the chemical/physical properties of the precipitants. Although TDPI has a melting point of greater than 100° C., it tends to precipitate in liquid form when precipitated from solutions via addition of a non-solvent. This liquid phase solidifies after some time and becomes a compact solid product. The only process technology which can change this behaviour is the use of very heavy-duty stirrer systems, e.g. screw kneaders. Normal stirrers such as those used in stirred tanks are insufficient and cease to operate. Precipitation of TDPI in a stirrable, crystalline and filterable form, without passing through the liquid phase, requires a very sophisticated process of precipitant addition.

A second difficulty is that there are very few remaining chlorinated hydrocarbons that can be used industrially. One of these is dichloromethane. If the system used comprises dichloromethane as reaction solvent and methanol as precipitant, distillative separation becomes impossible because an azeotropic system forms; its constitution being 93% of $CH_2Cl_2$; 7% of $CH_3OH$, with a boiling point of 38° C. This mixture cannot, moreover, be used as solvent for subsequent batches because the methanol reacts with bromine and liberates highly corrosive hydrogen bromide.

Petroleum spirit or heptane also reacts with bromine, and an essential requirement of the process therefore has to be clean distillative isolation of the precipitant from dichloromethane. Experience has shown that the content of precipitant in the dichloromethane should not exceed 0.1%.

It has also been found that repeated use leads to an increase in the concentration in the precipitant of by-products which, on standing, give tacky deposits and require repeated cleaning of containers, and also distillation of the actual precipitant.

A process which takes into account the problems described above should therefore have the following features:
- reaction of triallyl isocyanurate with bromine in dichloromethane
- addition of a precipitant which does not form an azeotrope with dichloromethane
- crystallization of TDPI
- filtration and washing (with precipitant)
- drying
- separation of dichloromethane from precipitant by means of multistage distillation
- distillation of precipitant as required by degree of contamination
- discarding of by-products.

Finally, the large-scale preparation of TDPI is relatively expensive and a more cost effective procedure would be highly desireable.

DESCRIPTION OF THE INVENTION

An objective of the present invention is to provide a process which can be used to prepare solid TDPI without the disadvantages of prior art processes and which is both efficient and relatively inexpensive for large-scale production. The process should also offer economic and environmental advantages in industrial synthesis.

These objectives are acheived by a process for the preparation of solid precipitates of tris(2,3-dibromopropyl) isocyanurate, in which the compound is brought into contact, in an organic solvent, with an adsorbent which is porous and solid under reaction conditions, which has a BET surface area of from 50 to 700 $m^2/g$, and which is isolated.

A particular advantage of this procedure is that TDPI, which is difficult to crystallize, can be converted quantitatively into solid material. The resultant precipitates are non-tacky and can very easily be freed from the solvent due to the surprising solidification of the TDPI on the adsorbent. Thus, the process eliminates problems associated with the handling of liquid precipitants. Concentrations of 80% or more of TDPI are obtainable with porous adsorbents. Although the TDPI solidifies on the adsorbent, after a short time two solid phases are present, but, surprisingly, no migration or separation is observed.

The porous adsorbent for initiating the formation of solid precipitates of TDPI may, in principle, be any material available to a person skilled in the art, as long as it maintains a solid consistency under process conditions. Advantageous materials are those which do not react with the reagents and solvents used. Preferred materials include polymer granules, silica, and silicates.

Polymer granules are microporous polymeric products which are produced from commercially available polymers, such as PP, PE, and PA. The microporous structures act like miniature sponges and can take up more than their own weight of liquids via capillary action. These granules remain surprisingly dry and flowable during use. By way of example, granules of this type are produced under the trademark Accurel® by Membrana GmbH, Obernburg, Germany. It is particularly advantageous to use granulated, microporous polypropylene, because TDPI is mainly used as flame retardant in items manufactured from polypropylene.

Silicas are autocondensation products of orthosilicic acids ($H_4SiO_4$) with the general formula $(SiO_2)_m \cdot xH_2O$. Their large-scale industrial preparation entails precipitation of alkali metal silicate solutions with acids, and as a result, they are called precipitated silicas. Fine-particle products can also be obtained via combustion of $SiCl_4$ in a stream of hydrogen and oxygen. Precipitated silicas are preferably used for the absorption of TDPI. These products have BET surface areas of from 50 to 700 $m^2/g$. Silicas which can be used with advantage can be found in the product catalogues of, for example, Degussa.

Silicates are metal salts of orthosilicic acid and condensates thereof. Pulverulent calcium silicate can be used with advantage in the present invention.

The adsorbents used are intended to have a solid consistency under reaction conditions, i.e., the adsorbent is intended to have structural integrity at least over the period of adsorption and isolation, so that solid precipitates can be obtained. Because the adsorption process is advantageously carried out in the range of 0 to 100° C., preferably from 15 to 80° C. and very particularly preferably from 20 to 50° C., the adsorbent should have structural integrity over the abovementioned period at a temperature of at least 100° C.

As mentioned previously, the BET surface area of the adsorbents should be in the range of from 50 to 700 $m^2/g$, in order to give cost-effective results. The BET surface area can preferably be from 60 to 500 $m^2/g$ and particularly preferably from 80 to 200 $m^2/g$.

The presence of pores in the adsorbent is essential for the process. These pores should have an average pore diameter which permits the efficient penetration of TDPI into the adsorbent. Particularly advantageous materials are those whose average pore diameter is from 1 to 100 µm, preferably from 3 to 50 µm and very preferably from 5 to 20 µm. The pore diameter is determined to DIN 66133 and DIN 66134.

Organic solvents which may be used in the adsorption process are those which are inert towards the reagents present. Because the preparation process advantageously proceeds by way of free-radical bromination of triallyl isocyanurate, preference is to be given to organic solvents which can also be used for free-radical bromination reactions. In particular, these are solvents selected from the group consisting of: dichloromethane, tetrachloroethane, acetic acid, carbon tetrachloride, chloroform or mixtures of the same.

Preferably, the porous adsorbent is added to the finished TDPI reaction solution to precipitate the material. In principle, it is also possible to use the reverse procedure. The process takes place at temperatures which permit efficient isolation of TDPI, in particular within the temperature limits stated above. Once the adsorbent has been added, stirring is generally continued for a time sufficient to complete adsorption of TDPI on the adsorbent. The material may then be isolated and dried. For isolation, the reaction solution may be removed by distillation and the remaining solid precipitate may be further processed. The present invention likewise provides a solid which is obtainable as described immediately above. This solid is composed of a solid precipitate of tris(2, 3-dibromopropyl)isocyanurate, which has been bound by adsorption on the solid porous adsorbent.

The solid described above may be used for providing flame retardancy to plastic products. In one preferred embodiment, the form in which the solid is incorporated into such products is that obtainable after isolation and drying. Preferably, the solid is used to provide flame retardancy to polypropyene, polyethylene and polystyrene and to the products produced therefrom.

As stated, the inventive process can be used to produce TDPI (which is otherwise difficult to isolate in solid form), in practically quantitative yield and purity via adsorption on porous adsorbents. The product is in a form which permits improved isolation and allows for simple further processing of the materials into articles. The good handling characteristics of the product, and the rapid and simple conduct of the process, especially on a large scale, are essential advantages of the inventive process and the solid produced.

EXAMPLES

Example 1

60 g of triallyl isocyanurate form an initial charge in 150 ml of dichloromethane in a flask, and 114 g of bromine are added in such a way as to give gentle reflux. Stirring is continued for 1 h until the bromine colour has disappeared, and 170 g of porous polypropylene (e.g. Accurel® MP 100 or MP 1000) are introduced. The dichloromethane is driven off via application of a slight vacuum at about 40° C., and the residue comprises about 50% by weight of TDPI in the form of practically colourless, free-flowing granules, with no formation of tacky deposits.

Alternatively, the reaction solution may be added to an initial charge of polymer, and the solvent may be evaporated simultaneously.

Example 2

A brominated triallyl isocyanurate solution, prepared according to Example 1, is added to an initial charge of precipitated silica (e.g., Sipernat 50, produced by Degussa AG), and the solvent is removed by distillation.

The residue comprises a non-tacky and free-flowing TDPI preparation comprising 70% by weight.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A process for preparing solid precipitates of tris(2,3-dibromopropyl) isocyanurate (TDPI), comprising:
   a) bringing TDPI into contact with an adsorbent in an organic solvent for a time sufficient to form said precipitates of TDPI, wherein said adsorbent:
      i) is porous and solid under the conditions of said process; and
      ii) has a BET surface area of from 50 to 700 $m^2/g$;
   b) isolating the precipitates formed in step a) from said organic solvent.

2. The process of claim 1, wherein said precipitates solidify on said adsorbent to form a solid mixture of TDPI precipitate bound by adsorption to said adsorbent and said solid mixture is isolated from said organic solvent.

3. The process of claim 1, wherein said adsorbent is selected from the group consisting of: silica; polymer granules; and silicates.

4. The process of claim 3, wherein said adsorbent has a solid consistency at a temperature $\geqq 100°$ C.

5. The process of claim 1, wherein said adsorbent has an average pore diameter of from 1 to 100 μm.

6. The process of claim 5, wherein said adsorbent has an average pore diameter of from 5 to 20 μm.

7. The process of claim 1, wherein said organic solvent comprises one or more solvents selected from the group consisting of: dichloromethane, tetrachloromethane, acetic acid, carbon tetrachloride, chloroform.

8. The process of claim 1, wherein said process is carried out at a temperature of 0 to 100° C.

9. The process of claim 8, wherein said process is carried out at a temperature of 20 to 50° C.

10. The process of claim 1, wherein said adsorbent has a BET surface area of from 80 to 200 $m^2/g$.

11. A TDPI precipitate formed by the process of claim 1.

12. The TDPI precipitate of claim 11, wherein said TDPI precipitate is bound by adsorption to said adsorbent.

13. A plastic product comprising the TDPI precipitate of claim 11.

14. A process for preparing solid precipitates of tris(2,3-dibromopropyl) isocyanurate (TDPI), comprising:
    a) bringing TDPI into contact with an adsorbent in an organic solvent for a time sufficient to form said precipitates of TDPI, wherein said precipitates solidify on said adsorbent to form a solid mixture of TDPI precipitate bound by adsorption to said adsorbent and wherein said adsorbent:
        i) has a BET surface area of from 50 to 700 $m^2/g$;
        ii) is selected from the group consisting of: silica; polymer granules; silicates;
        iii) has a solid consistency at a temperature $\geqq 100°$ C.; and
        iv) has an average pore diameter of from 1 to 100 μm;
    b) isolating said solid mixture formed in step a) from said organic solvent.

15. The process of claim 14, wherein said organic solvent comprises one or more solvents selected from the group consisting of: dichloromethane, tetrachloromethane, acetic acid, carbon tetrachloride, chloroform.

16. The process of claim 15, wherein said process is carried out at a temperature of 0 to 100° C.

17. The process of claim 16, wherein said process is carried out at a temperature of 20 to 50° C.

18. The process of claim 15, wherein said adsorbent has a BET surface area of from 80 to 200 $m^2/g$.

19. The process of claim 15, wherein said adsorbent has an average pore diameter of from 1 to 100 μm.

20. The process of claim 19, wherein said adsorbent has a BET surface area of from 80 to 200 $m^2/g$.

\* \* \* \* \*